United States Patent [19]

Kim et al.

[11] Patent Number: 5,189,082
[45] Date of Patent: Feb. 23, 1993

[54] IMIDE EPOXY RESINS FOR SEALING SEMICONDUCTOR ELEMENTS

[75] Inventors: Whan G. Kim, Seoul; Tai Y. Nam, Kyungki-do, both of Rep. of Korea

[73] Assignee: Cheil Industries, Inc., Taegu-si, Rep. of Korea

[21] Appl. No.: 803,041

[22] Filed: Dec. 6, 1991

[30] Foreign Application Priority Data

Sep. 26, 1991 [KR] Rep. of Korea .................. 91-16824

[51] Int. Cl.$^5$ ................ C08G 59/26; C08G 59/32; C08G 73/06; C08G 73/10
[52] U.S. Cl. .................................. 523/443; 523/466; 525/481; 525/482; 525/484; 528/96; 549/551; 549/553
[58] Field of Search ............... 523/443, 466; 525/482, 525/484, 481; 528/96

[56] References Cited

U.S. PATENT DOCUMENTS

| | | | |
|---|---|---|---|
| 4,555,563 | 11/1985 | Hefner, Jr. et al. | 528/96 |
| 4,600,769 | 7/1986 | Kumar et al. | 528/170 |
| 4,720,521 | 1/1988 | Spielvogel et al. | 524/862 |
| 4,806,430 | 2/1989 | Spielvogel et al. | 428/450 |
| 4,861,810 | 8/1989 | Dewhirst | 528/124 |

FOREIGN PATENT DOCUMENTS

| | | |
|---|---|---|
| 54-142298 | 11/1979 | Japan . |
| 58-89619 | 5/1983 | Japan . |
| 58-215452 | 12/1983 | Japan . |
| 59-64660 | 4/1984 | Japan . |
| 59-227918 | 12/1984 | Japan . |
| 59-227924 | 12/1984 | Japan . |
| 62-477 | 1/1987 | Japan . |
| 62-7719 | 1/1987 | Japan . |
| 62-7723 | 1/1987 | Japan . |
| 62-53324 | 3/1987 | Japan . |
| 62-106920 | 5/1987 | Japan . |
| 62-227917 | 6/1987 | Japan . |
| 62-260817 | 11/1987 | Japan . |
| 62-268132 | 11/1987 | Japan . |
| 62-270618 | 11/1987 | Japan . |
| 63-230725 | 9/1988 | Japan . |
| 63-230728 | 9/1988 | Japan . |

OTHER PUBLICATIONS

J. Macromol. Sci.-Chem., A 22(8), pp. 1101-1107 (1985), "Bisaspartimide-Diamines as Curing Agents for Epoxy Resins".
Kinjo et al., "Epoxy Molding Compounds . . . ", from Advances in Polymer Science 88, Springer-Verlag Berling Heid. 1989, pp. 1-48.

Primary Examiner—Robert E. Sellers
Assistant Examiner—Frederick Krass
Attorney, Agent, or Firm—Leydig, Voit & Mayer

[57] ABSTRACT

The present invention relates to novel epoxy resin compositions for sealing semiconductor elements, which comprise 0.1 to 20.0% by weight of imide-epoxy resins represented by the general formula (I) together with epoxy resins, curing agents, curing promoters and plasticizers, and which has improved heat resistant and moisture resistant properties:

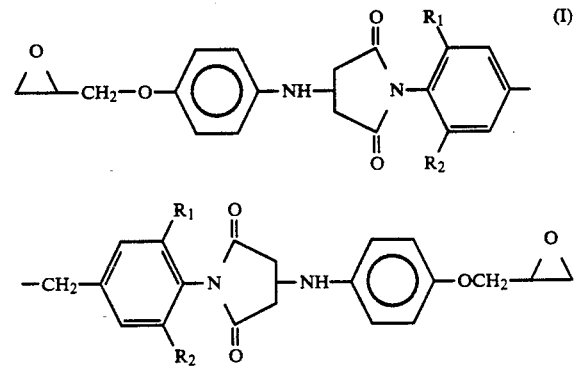

wherein,
$R_1$ and $R_2$ represent H or $-CH_2)_n CH_3$ group, and
n represents an integer of 0 or 1.

14 Claims, No Drawings

IMIDE EPOXY RESINS FOR SEALING SEMICONDUCTOR ELEMENTS

FIELD OF THE INVENTION

The present invention relates to novel imide-epoxy resins, a process of preparation, and epoxy resin composition for sealing semiconductor compositions. More particularly, the present invention is directed to imide-epoxy resins and to epoxy resin compositions containing same in which the epoxy group is incorporated into bismaleimide, a process for producing imide-epoxy resins, and epoxy resin compositions having low stress, high heat resistance and high moisture resistant properties for sealing semiconductor elements.

BACKGROUND OF THE INVENTION

Recently, owing to the tendency of the electric and electronic components and sets to be small and thin, IC and LSI packages have been rapidly varied. Particularly, in spite of the fact that the size of chip has become larger, the package has to become thin and small and has high pin numbers. The mounting technology has also varied with surface mounting technology. Recently, a Thin Small Out-line J-Bend Package (TSOJ), having about 1 mm of thickness, is being produced. TSOJ, which is a medium stage type between Small Out-line J-Bend Package (SOJ)/Quad Flat Package (QFP) and Tape Automated Bonding(TAB), will be used as a main type in the memory element field in the near future. According to the change of such a package, resin compositions for sealing semiconductor elements also concurrently requires strict low stress, high heat resistance and high moisture resistance over the prior art compositions.

A method for decreasing inner stress by adding plasticizers such as a modified silicone oil or CTBN(Japanese Laid-open Patent Publication Nos. (Sho) 63-230725; 62-7719; 62-106920; and 62-260817) and a method for lowering thermal expansion coefficient by increasing the amounts of fillers [Advances in Polymer Science 88, 1-48(1989)] are known as low stress techniques. However, such methods have serious problems such as lower heat resistance, moldability and abrasion of equipment.

Meanwhile, Although a method for improving heat resistance by using polyfunctional epoxy resins (Japanese Laid-open Patent Publication Nos. (Sho) 62-477 and 62-7719 and a method for improving heat resistance by using bismaleimide (Japanese Laid-open Patent Publication Nos. (Sho) 62-132961; 62-7723; 54-142298; and 58-215452) are well known, these methods have problems in that due to an increase of the glass transition temperature the moisture resistant property decreases. In addition, it has been suggested that maleimide be added to improve heat resistance (Japanese Laid-open Patent Publication Nos. (Sho) 62-53324 and 62-270618). It has been attempted to increase the thermal property of resin compositions by curing epoxy resins with reaction initiators having functional groups such as COOH, OH, NH, etc. at the terminal of imide backbone. However, there is an upper limit to the amount of imide which contributes to the improvement of the heat resistance property. Japanese Patent Publication Nos. (Sho) 58-215452; 58-89619; 59-64660; 59-227924; 62-227917; etc. disclose a method for reacting an amino group with an epoxy group in resin compositions, by initially reacting compounds having amino groups at the terminal position, for example, p- or m-aminophenol and diaminodiphenylmethane with a commercially available maleimide to obtain a prepolymer, and then adding it to resin compositions. However, this method has difficulties in controlling the degree of reaction and also has a limit in increasing the imide content. A method for increasing the heat resistant property by blending epoxy resins and amine compounds with polyfunctional polymaleimide to improve the curing property is also known. This method also has problems in storage stability at room temperature (20° to 30° C.) and difficulties in homogeneous curing reactions. Japanese Laid-open Patent Publication Nos. (Sho) 59-227918; 62-268132; 63-230728; etc., disclose modified curing agents, which are curing agents for epoxy resins and capable of reacting with both epoxy and maleimide by incorporating an allyl group into phenolnovolak resins, and curing agents having both hydroxy groups and allyl groups in the epoxy resins. Since the latter is prepared by incorporating an allyl group into phenol resins and then reacting the resulting product with epoxy resins, it is a complex and costly process.

Therefore, the object of the present invention is to provide novel imide-epoxy resins, wherein an epoxy group is incorporated into a bismaleimide which is useful for improving heat resistance to resin compositions and a process for preparing the same.

Another object of the present invention is to provide resin compositions in which an epoxy group is incorporated into a maleimide to impart low stress properties and high moisture and heat resistance for sealing super thin high integrated IC elements.

SUMMARY OF THE INVENTION

The gist of the present invention to achieve the above objects resides in imide-epoxy resins obtained by reacting a bismaleimide and a compound obtained from the reaction of p-aminophenol and epichlorohydrin in dimethylformamide solution, and epoxy resin compositions having improved heat resistance and comprising said imide-epoxy resins as additives in an amount of 5 to 50% by weight based on the weight of the total resin compositions, especially epoxy resin compositions for sealing semiconductor elements, which have good heat and moisture resistance and low stress properties and comprises said imide-epoxy resins in an amount of 0.1 to 20% by weight based on the weight of the total resin compositions.

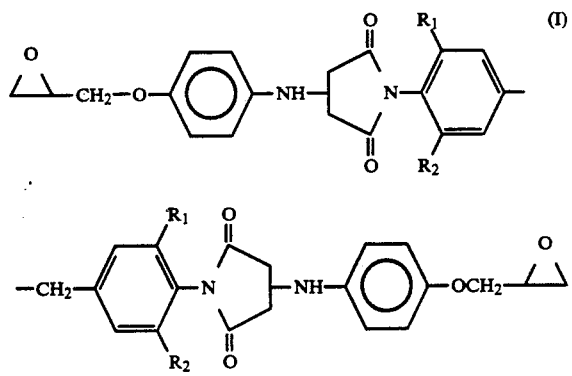

Wherein,
$R_1$ and $R_2$ denote H or $-(CH_2)_m CH_3$ group, and
n denotes an integer of 0 or at least 1.

DETAILED DESCRIPTION OF THE INVENTION

Hereinafter, the present invention will be described in detail.

Synthesis of the Imide-Epoxy Resins

The imide-epoxy resins of the present invention can be synthesized via the following reaction schemes.

① NH$_2$—⟨⟩—OH + ClCH$_2$CH—CH (epoxide) ⟶ NH$_2$—⟨⟩—O CH$_2$CH—CH$_2$ (epoxide)    (III)

② [bismaleimide structure] (II) + 2 NH$_2$—⟨⟩—O CH$_2$CH—CH$_2$ (epoxide) ⟶    (II)

[imide-epoxy resin structure]    (I)

wherein,
R$_1$ and R$_2$ stand for H or —(CH$_2$)$_n$CH$_3$ group, and
n stands for an integer of 0 or at least 1.

The reaction can be carried out by dissolving p-aminophenol and epichlorohydrin in dimethylformamide, while maintaining the suitable temperature of below 10° C., and adding 97% NaOH under a nitrogen atmosphere. The solvent and by-products are removed from the reactant to obtain a product in which an epoxy group is incorporated into a hydroxy group of aminophenol (Reaction scheme 1). The resultant product and bismaleimide of the general formula (II) are dissolved in DMF completely, and then the mixture is allowed to react for several hours under a nitrogen atmosphere, while maintaining the temperature of 150° to 200° C. The resultant product is separated with ice water, and the solvent is removed to give imide-epoxy resins of the general formula (I) as a yellow powdery material (Reaction scheme 2).

Maleimide compounds to be used in the preparation of said imide-epoxy resins include, for example, MB3000, MB3000H, MB7000, etc. (manufactured by Mitsubishi Petrochemical Co., Ltd.), MP2000X, MP256 and 276 of polyfunctional maleimides, and Bestlex A-4L (manufactured by Sumitomo Chemical Company, Limited).

The resulting imide-epoxy resins of the present invention have excellent reactivity and heat resistant properties, and thus, can be utilized for preparing heat resistant epoxy resin compositions and low stress, high heat and high moisture resistant epoxy resin compositions for sealing semiconductor elements.

Heat Resistant Epoxy Resin Compositions

The present invention provides new heat resistant epoxy resin compositions comprising said imide-epoxy resins as reactivity- and heat resistant-enhancers. That is, the present invention provides heat resistant resin compositions wherein 5 to 50% by weight of imide-epoxy resins of the general formula (I) are added to resin compositions having epoxy resins as a basic resin when using 5 to 50% by weight of the compound of formula (I) as additives in all of the compositions consisting of epoxy resins as basic resins, resin compositions having good heat resistant properties can be obtained.

An example of the preferable composition ratio is as follows:

Epoxy resins: 45 to 65% by weight
Imide-epoxy resins of the formula (I): 5 to 50% by weight
Curing agents: 25 to 35% by weight
Curing catalysts: 0.1 to 3% by weight Preferable epoxy resins to be used in the present invention include Bisphenol A resins and cresol-novolak epoxy resins, for example, Epicot 827, 828, 834, 864, 1001, 1004, 1007, 1031 (manufactured by Shell Petrochemical Epoxy Co., Ltd.) and EOCN 1020, 1025, 1027, 1029, 103S, 104S (manufactured by Japan Chemical Co., Ltd.). Preferable curing agents include phenol-novolak resins, and curing catalysts include tertiary amines, tertiary amine salts, quarternary ammonium salts, imidazole derivatives and organic phosphine compounds.

The amount of imide-epoxy resins of formula (I), which are the main additives in the present invention, is 5 to 50% by weight, preferably 8 to 30% by weight, of the resin compositions. When the amount is less than 5% by weight, the heat resistant property of the compositions will only be slightly improved, and when the amount is greater than 50% by weight, the compositions will exhibit poor stress resistance and be costly to produce.

Heat resistant resin compositions of the present invention can be obtained by mixing the constituents at a suitable ratio based on the constitutional example, heating the mixture at a temperature of 120° C. to 200° C. to effect the curing reaction, and post-curing the cured products at 200° C. for several hours. The resulting resin compositions of the present invention exhibit excellent heat resistance.

Epoxy Resin Compositions for Sealing Semiconductor Elements

The present invention also provides low stress, high heat resistant and high moisture resistant epoxy resin compositions for sealing semiconductor elements, comprising cresol-novolak epoxy resins, phenolnovolak type curing agents, curing promoters and inorganic fillers, which are characterized in that imide-epoxy resins of formula (I) are added to cresol-novolak epoxy resins.

Epoxy resin compositions for sealing semiconductor elements of the present invention comprise epoxy resin compositions of o-cresol-novolak epoxy resins and imide-epoxy resins of formula (I) as basic resins, phenol novolak type curing agents, triphenylphosphine belonging to organic phosphine compounds as curing promoters, high purity fused silica as fillers, epoxy-modified silicone oil as modifiers, mold release agents, colorants, and organic or inorganic flame retardants, or the like as known by those skilled in the art.

The preferable constitutional example of the present resin compositions is as follows:

Cresol-novolak type epoxy resins: 0.1 to 20% by weight
Imide-epoxy resins: 0.1 to 20% by weight
Curing agents: 1.0 to 10.0% by weight
Curing promoters: 0.1 to 1.0% by weight
Coupling agents: 0.5 to 2.0% by weight
Colorants: 0.1 to 0.5% by weight
Fillers: 65.0 to 85.0% by weight
Mold release agents: 0.1 to 1.0% by weight
Organic flame retardants: 1.0 to 5.0% by weight
Inorganic flame retardants: 0.5 to 3.0% by weight
Plasticizers: 0.5 to 5.0% by weight The above constitution is most preferable for the present resin compositions. Epoxy resin to be used in the present invention include good heat resistant o-cresol-novolak resins, especially high purity epoxy resins having a 190 to 220 epoxy equivalent weight and below 10 ppm of impurity content. As to the curing agents, phenol-novolak resins, which have a softening point of 100° to 120° C., a 100 to 120 hydroxy equivalent weight and below 10 ppm of impurity content, are used.

Polyfunctional epoxy resins to be used specifically in the present invention include bismaleimide-based imide-epoxy resins of formula (I), and the amount to be used is preferably between 0.1 and 20.0% by weight, more preferably between 1.0 and 10.0% by weight, based on the total weight of the compositions. If the amount is less than 0.1% by weight, the heat resistant and moistare resistant properties are very poor, and if the amount is greater the 20% by weight, phenomena such as resin bleed and mold fouling occur. Thus, moldability decreases and problems related to the gel time and conditions at post-curing and cost result.

It is preferable to use high purity fused silica as a filler in the present invention. Fused silica having a particle size of 10 to 30 μm is preferable. As curing promoters, amines, imidazole derivatives and organic phosphine compounds are commercially used. In the present invention, it is preferable to use triphenylphosphine, and 2-methylimidazole and 2-methyl-4-ethylimidazole as organic phosphine compounds and imidazole derivatives, respectively.

Coupling agents to be used in the surface treatment of inorganic fillers include silane-based coupling agents. It is most preferable to use γ-glycidoxypropyltrimethoxysilane.

As plasticizers, silicone rubber or epoxy-modified silicone oil is used. Plasticizers, which are used in the present invention so as to increase compatibility according to the high integration of semiconductor, include an adduct of phenol-novolak resins and epoxy-modified silicone oil.

Epoxy resin compositions of the present invention utilize 0.1 to 1.0% by weight of carnauba wax or Montan wax as a mold release agent, 0.1 to 0.5% by weight of carbon black as a colorant, brominated epoxy resin as an organic flame retardant, and antimony trioxide as an inorganic flame retardant.

The compositions of the present invention can be prepared by surface treating inorganic fillers with coupling agents, homogeneously mixing them with the remaining components in a Henschel mixer, or other premixer, melt mixing at 90° to 110° C. for about 5 to 20 min. using a kneader or roll mill, cooling and pulverizing.

When sealing semiconductor elements with the powdery compositions, the compositions is tableted in the tableting machine. The tableted resin compositions is pre-heated with high frequency preheater, and molded with a molding press at 170° to 180° C. for 90 to 120 sec. to seal the semiconductor elements.

As mentioned above, the resin compositions produced by the present invention includes imide-epoxy resins of formula (I) in available cresol-novolak epoxy resins so as to improve heat resistant and moisture resistant properties, and can provide resin compositions suitable for sealing a super-thin, high integrated semiconductor, due to the high glass transition temperature and improved moisture resistance over the prior art compositions.

Hereinafter, the present invention will be explained in detail by virtue of examples, which should be construed to limit the scope of the present invention.

EXAMPLES

Synthesis of Imide-Epoxy Resins

Equivalent mole ratios of p-aminophenol and epichlorohydrin are dissolved in DMF, and the mixture is reacted for 2 hours under a nitrogen atmosphere with the addition of 97% NaOH dissolved in DMF, while maintaining the temperature at 10° C. The solvent and by-products are removed, bismaleimides MB3000 and MB7000 (manufactured by Mitsubishi Petrochemical Co., Ltd.) having the following formulae are added to the resultant product (with the mole ratio of resultant product/bismaleimide of 2/1) to dissolve thoroughly, and then reacted at 180° C. for 4 hours in a nitrogen atmosphere. The resulting product is washed with cold water, and dried to obtain imide-epoxy resins as a yellow powder.

MB3000:
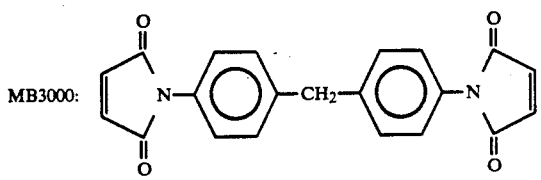

-continued

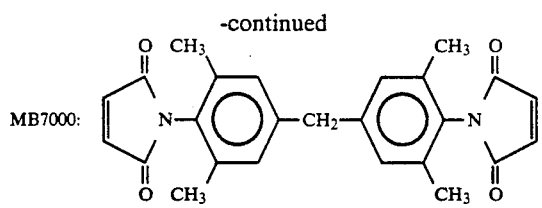

MB7000:

EXAMPLES 1-5

Heat Resistant Epoxy Resin Compositions

Constitutional components having the composition set forth in Table 1 are mixed in a Henschel mixer to give pre-compositions in the form of powders, and the pre-compositions are cured for 3 hours at 120° C., and for 4 hours at 200° C. to obtain heat resistant resin compositions.

Physical properties of the heat resistant resin compositions are listed on Table 1. From Table 1, it can be seen that the thermal property of the compositions obtained from these examples is superior to that of Comparative Examples 1 and 2.

COMPARATIVE EXAMPLES 1-2

Comparative Examples 1-2 are conducted in a manner similar to Examples 1-5 except that bismaleimide (MB3000) was used in place of imide-epoxy resins. The physical properties are also shown in Table 1.

TABLE 1

(Unit: % by weight)

|  | Examples | | | | | Comparative Examples | |
|---|---|---|---|---|---|---|---|
|  | 1 | 2 | 3 | 4 | 5 | 1 | 2 |
| o-cresolnovolak type epoxy resins (EOCN1020) | 70 | 70 | 70 | 70 | 70 | 70 | 70 |
| Phenolnovolak (PSM4261) | 40 | 40 | 40 | 40 | 40 | 40 | 40 |
| Triphenyl-phospine | 1.5 | 1.5 | 1.5 | 1.5 | 1.5 | 1.5 | 1.5 |
| Imide-epoxy resins (Synthesis example | | | | | | | |
| (I) | 10 | — | — | — | — | — | — |
|  | — | 20 | — | — | — | — | — |
|  | — | — | 30 | — | — | — | — |
| (II) | — | — | — | 10 | — | — | — |
|  | — | — | — | — | 20 | — | — |
| Bismaleimide | — | — | — | — | — | 10 | — |
| (MB3000) | — | — | — | — | — | — | 20 |
| HDT (°C.) | 201 | 218 | 236 | 205 | 220 | 200 | 210 |
| TGA (°C.) | | | | | | | |
| 5 wt % loss | 320 | 339 | 351 | 318 | 340 | 315 | 335 |
| 10 wt % loss | 330 | 346 | 360 | 332 | 350 | 333 | 351 |
| Tg (°C.) | 175 | 201 | 205 | 170 | 203 | 170 | 198 |

*HDT: Measured by ASTM-D-648
*TGA: Stanton Redcraft STA 1500(measured at 10° C./min.)
*Tg: Stanton Redcraft TMA 1000(measured at 10° C./min.)
*Imide-epoxy resins
I: made by MB3000
II: made by MB7000

EXAMPLES 6-9

Resin Compositions for Sealing Semiconductor Elements

Constitutional components of which the compositions are set forth in Table 2 are homogeneously mixed in a Henschel mixer to give powdery precompositions. The precompositions are kneaded for 10 min. at 100° C. with a kneader, cooled and pulverized to obtain epoxy resin mold material. Physical properties of the obtained epoxy resin compositions are measured as follows. The results are presented in Table 3.

1) Spiral flow: Measured at a molding temperature of 175° C. and 70 kg. f/cm of molding pressure using a mold prepared according to EMMI standard
2) Tg: Measured with TMA equipment
3) E (Kg. f/mm$^2$): Measured with UTM according to ASTM D190
4) Thermal expansion coefficient $\alpha(°C.^{-1})$: Measured according to ASTM D696
5) Moisture content(%): Measured the saturated moisture content, after the molded article stood for 48 hours at 121° C., 2 atm. vapor.
6) Resistance to cracking: Measured from the crack numbers generated in the 2,000 times thermal impact test on a molded chip under the test conditions having one cycle of −55° C., 30 min. and 150° C., 30 min.

COMPARATIVE EXAMPLE 3

Comparative Example 3 was carried out in a manner similar to Examples 6-9, according to the following compositions (disclosed in Table 2), and physical properties are measured. The results are shown in Table 3.

TABLE 2

| Components | Example 6 | Example 7 | Example 8 | Example 9 | Comparative Example 3 |
|---|---|---|---|---|---|
| Cresol-novolak epoxy resins | 14.57 | 13.07 | 8.07 | 3.07 | 15.07 |
| Imide-epoxy resins (MB7000: Synthesis example) | 0.5 | 2.0 | 7.0 | 12.0 | — |
| Phenolnovolak(curing agent) | 5.83 | 5.83 | 5.83 | 5.83 | 5.83 |
| Triphenylphospine (curing promoter) | 0.38 | 0.38 | 0.38 | 0.38 | 0.38 |
| Fused silica | 73.8 | 73.8 | 73.8 | 73.8 | 73.8 |
| Plasticizers | 1.15 | 1.15 | 1.15 | 1.15 | 1.15 |
| Brominated epoxy resin (organic flame retardant) | 1.30 | 1.30 | 1.30 | 1.30 | 1.30 |
| KBM 403(Shin-etsu Chemical Co., Ltd.; coupling Agent) | 1.11 | 1.11 | 1.11 | 1.11 | 1.11 |
| Carnauba wax (mold release agent) | 0.23 | 0.23 | 0.23 | 0.23 | 0.23 |
| Sb$_2$O$_3$ (inorganic flame retardant) | 0.85 | 0.85 | 0.85 | 0.85 | 0.85 |

TABLE 2-continued

| Components | Example 6 | Example 7 | Example 8 | Example 9 | Comparative Example 3 |
|---|---|---|---|---|---|
| Carbon Black(colorant) | 0.26 | 0.26 | 0.26 | 0.26 | 0.26 |

TABLE 3

| Contents | Example 6 | Example 7 | Example 8 | Example 9 | Comparative Eample 3 |
|---|---|---|---|---|---|
| Spiral flow(in.) | 45 | 45 | 43 | 40 | 45 |
| Tg (°C.) | 185 | 190 | 195 | 203 | 170 |
| α(× 10⁻⁵/°C.) | 1.4 | 1.3 | 1.2 | 1.1 | 1.7 |
| E(kgf/mm²) | 1200 | 1200 | 1250 | 1300 | 1200 |
| Moisture content (%) | 0.45 | 0.43 | 0.40 | 1.38 | 0.5 |
| *Resistance to cracking (2000 times) | 2/600 | 1/600 | 0/600 | 0/600 | 6/600 |

*In the values showing the resistance to cracking, the denominator represents the number of samples and the numerator represents the failure numbers.

As can be seen from the results listed in Table 3, resin compositions of the present invention have superior moldability, heat resistant and moisture resistant properties over the comparative Examples. Accordingly, the resulting resin compositions for sealing semiconductor elements have highly improved resistance to cracking.

What is claimed is:

1. An epoxy resin composition for sealing semiconductor elements comprising cresol-novolak epoxy resins, curing agents, curing promoters and inorganic fillers, including imide-epoxy resins represented by the general formula:

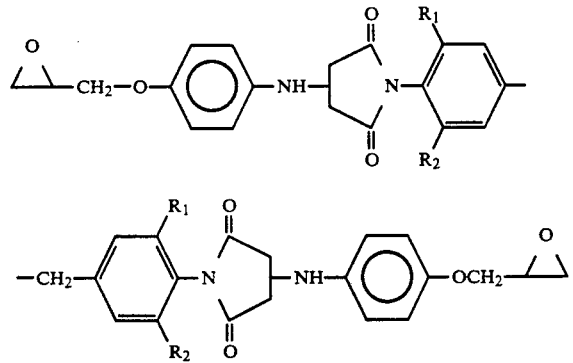

wherein, $R_1$ and $R_2$ represent H or a —$(CH_2)_n$—$CH_3$ group and n=0 or 1.

2. An epoxy resin composition claimed in claim 1, wherein the imide-epoxy resins are present in an amount of from 0.1 to 20.0% by weight on the basis of the total weight of the composition.

3. An epoxy resin composition according to claim 1, wherein said curing agent is a phenol novolak curing agent.

4. An epoxy resin composition according to claim 1 wherein said curing promoter is an organic phosphine curing promoter.

5. An epoxy resin composition according to claim 1 wherein n=0.

6. An epoxy resin composition according to claim 1 wherein n=1.

7. An epoxy resin composition according to claim 1 wherein said curing promoter is an amine or imidazole.

8. An epoxy resin composition according to claim 1 wherein said curing promoter is triphenylphosphine.

9. An epoxy resin composition according to claim 1 wherein said curing promoter is 2-methylimidazole.

10. An epoxy resin composition according to claim 1 wherein said curing promoter is 2-methyl-4-ethylimidazole.

11. An epoxy resin composition according to claim 1 wherein said inorganic filler is fused silica.

12. An epoxy resin composition according to claim 1 wherein said composition further includes at least one flame retardant.

13. An epoxy resin composition according to claim 1 wherein $R_1$ and $R_2$ represent H.

14. An epoxy resin composition according to claim 1 wherein said curing agent is a phenol-novolak curing agent, said curing promoter is triphenylphosphine, said filler is fused silica, and said imide-epoxy resin is present in an amount of from 0.1 to 20.0%, by weight, of the total weight of the composition.

* * * * *